United States Patent [19]
Bayless et al.

[11] Patent Number: 5,885,671
[45] Date of Patent: Mar. 23, 1999

[54] POLYOXYALKYLENE GLYCOL GELATIN CAPSULE FILL FORMULATIONS COMPRISING CROSSLINKED CARBOXYLIC COPOLYMERS

[75] Inventors: Ronnie E. Bayless, Plant City, Fla.; Dennis Laba, Langhorne; William Reynolds, Newton, both of Pa.

[73] Assignee: R.P. Scherer North America, Clearwater, Fla.

[21] Appl. No.: 895,003

[22] Filed: Jul. 17, 1997

[51] Int. Cl.⁶ ............... B32B 5/16; B32B 9/02; B32B 9/04; B32B 15/02
[52] U.S. Cl. .......... 428/34.1; 428/35.7; 428/402.2; 428/402.21; 428/402.22
[58] Field of Search ............... 428/34.1, 35.7, 428/402.2, 402.21, 402.22

[56] References Cited

U.S. PATENT DOCUMENTS

| | | | |
|---|---|---|---|
| 4,634,606 | 1/1987 | Skogg | 427/256 |
| 5,254,379 | 10/1993 | Kotsiopoulos et al. | 428/35.7 |
| 5,393,054 | 2/1995 | Rouffer | 273/58 H |
| 5,416,158 | 5/1995 | Santhanam et al. | 524/760 |

*Primary Examiner*—Nathan M. Nutter
*Attorney, Agent, or Firm*—McDonnell Boehnen Hulbert & Berghoff

[57] ABSTRACT

Disclosed are fill compositions suitable for carrying pigment and encapsulation within gelatin capsules comprising:

(a) a polyoxyalkylene glycol having a mean molecular weight of from about 200–500;
(b) glycerol;
(c) water;
(d) an oleaginous material;
(e) a carboxylic copolymer; and
(f) a neutralizing agent for the carboxylic polymer in an amount effective to neutralize at least about 75% of the carboxylic acid groups on the polymer. Also disclosed are gelatin capsules containing sych compositions and methods for preparing the fill compositions.

22 Claims, No Drawings

POLYOXYALKYLENE GLYCOL GELATIN CAPSULE FILL FORMULATIONS COMPRISING CROSSLINKED CARBOXYLIC COPOLYMERS

BACKGROUND OF THE INVENTION

1. Field of the Invention

This invention relates to gelatin capsules and fill materials therefore. More specifically, the invention relates to gelatin capsules and fill materials suitable therefore where the fill materials contain polyethylene glycol and dye, pigment, or various cosmetic materials. It further relates to methods for preparing such fill materials and gelatin capsules.

2. Description of Related Art

Soft gelatin capsules (softgels) have been employed for the efficient and convenient delivery of a variety of substances for numerous different uses. For example, cosmetics, pharmaceuticals, and dyes or pigments have been encapsulated into soft gelatin capsules.

A specific use for dye-filled soft gelatin capsules is as paint-filled gelatin capsules, i.e., paintballs. Paint-filled softgels have found use as markers for trees (see U.S. Pat. No. 3,861,943) and as target shooting capsules for use with air powered rifles or handguns (see U.S. Pat. No. 4,656,092).

Conventional technology for manufacturing paintballs relies on the use of high molecular weight polyethylene glycols (PEG) as a thickener for the fill composition containing the dye. However, the use of such PEGs in paintballs is undesirable since it adds processing steps and the need for heat to melt the PEG thickener. For use in paintballs and other gelatin capsules as a component of the fill material, high molecular weight PEG must be melted and subsequently combined while hot with the remaining fill components. The resulting hot fill material must be cooled slowly and carefully, generally over a period of about 48 hours. Hot fill material cannot be used to fill soft gelatin capsules made with the rotary die process; gelatin capsules made with hot fill material have various problems including the lack of good seals since the addition of the fill is essentially concurrent with seal formation. Moreover, imprecise cooling typically results in defective fill material product.

The heating process is unattractive since it demands long processing times and large amounts of energy. In addition, the resulting products are generally suitable for use in limited temperature ranges since the high molecular weight PEG loses its ability to act a thickener at low temperatures and nearly solidifies at low temperatures. The proper stability of the fill material is necessary to produce a capsule projectile that will have a reliable trajectory upon being shot.

High molecular weight PEG also results in capsule projectiles that tend to increase size at low temperature as the fill materials, which typically include water, freeze. The resulting projectiles cause damage of the guns used to shoot the capsules, an obvious problem which can also injure the user of the gun.

Consequently, there is a need for fill materials suitable for use in gelatin capsules that are also capable of carrying a pigment where the fill material is not based on a high molecular weight polyethylene glycol. Suitable fill material compositions must be such that they (1) maintain their uniform character after filling into gelatin capsules and (2) are liquid at low temperature. In other words, the compositions must not separate at ambient temperature and not become too hard at temperatures near or below freezing.

U.S. Pat. No. 4,656,092, the disclosure of which is incorporated herein in its entirety, discloses target shooting capsules comprising a substantially spherical, nontoxic, soft elastic gelatin capsule containing a water washable, nontoxic fill material.

SUMMARY OF THE INVENTION

The present invention therefore provides fill materials for gelatin capsules that can be employed as projectiles that shoot reliably.

The invention provides fill compositions that typically have freezing points below about 0° C.

Thus, the fill compositions according to the invention can be prepared at about room temperature without the need for heating. They can also be prepared rapidly in relatively short periods of time.

Capsules prepared with the inventive fill compositions can be used as projectiles from guns over a wide temperature range without damage to the guns.

The fill materials of the invention also impart added strength to the finished capsules over a range of temperatures of from about 0° to 40° C.

Further purposes and objects of the present invention will appear as the specification proceeds.

With the foregoing and other objects in view, in a first aspect, the invention herein provides a composition suitable for carrying pigment and encapsulation within gelatin capsules comprising:

(a) a polyoxyalkylene glycol having a mean molecular weight of from about 200–500;

(b) glycerol;

(c) water;

(d) an oleaginous material;

(e) a carboxylic copolymer; and (f) a neutralizing agent for the carboxylic polymer in an amount effective to neutralize at least about 75% of the carboxylic acid groups on the polymer.

In another aspect, the invention provides gelatin capsules containing the fill materials. In this aspect, the fill compositions can be manufactured to contain a pigment and then filled into gelatin capsules. The resulting capsules can be used as projectiles, i.e., as paintballs.

In yet another aspect of the invention, there is provided a method for making the inventive fill materials.

Still another aspect of the invention is the use of the fill compositions to prepare cosmetic compositions for encapsulation within gelatin capsules. Such compositions may be creams or lotions and will contain, as active ingredients, various compounds such as fragrances, pigments, and vitamins such as vitamin A or E.

DETAILED DESCRIPTION OF THE PREFERRED EMBODIMENTS

The present invention concerns a composition suitable for carrying pigment and encapsulation within gelatin capsules comprising, by weight of the composition:

(a) from about 10–95% of a polyoxyalkylene glycol having a mean molecular weight of about 200–500;

(b) from about 1–5%, preferably about 2.5–3.5%, of glycerol;

(c) from about 1–85% of water;

(d) 0.05 to about 10% of oleaginous material;

(e) from about 0.1–3% of a carboxylic copolymer containing a crosslinking monomer selected from the group consisting of triallylisocyanurate, triallyl trimellitate and glyoxal bis(diallyl acetal) in combination with an ethoxylated glyceride surfactant ester with an HLB value greater than 10; and (f) a neutralizing agent for the carboxylic polymer in an amount effective to neutralize at least about 75% of the carboxylic acid groups on the polymer.

The polyoxyalkylene glycol is from about 10–95%, preferably 80–95%, and most preferably from about 85–95%, by weight of the fill composition. Preferred polyoxyalkylene glycols are polyethylene glycols having a mean molecular weight of about 300.

The compositions preferably contain from about 1–25%, and more preferably, from about 1–10%, by weight of water.

The oleaginous materials that can be used in the invention are any of a variety of oils. Representative oleaginous materials include $C_1$–$C_{22}$ straight or branched chain alkyl esters of straight or branched chain carboxylic acids having 12 to 22 carbon atoms, e.g., castor oil or jojoba oil, benzyl or $C_6$–$C_{22}$ straight or branched chain alkyl benzoates, glyceryl esters containing 8 to 22 carboxylic acid carbon atoms, e.g., fatty acid triglycerides, sorbitan esters, straight or branched alkyl esters of alkoxylated fatty acid esters, and fatty alcohols having from 10 to 22 carbon atoms, volatile hydrocarbons, e.g., mineral spirits, semisolid hydrocarbons such as petrolatum, and mineral oil.

Preferred oleaginous materials for use herein are mineral oil and isopropyl myristate. The oleaginous material is preferably incorporated in the composition in an amount of from about 0.05 to 10% by weight of the composition. More preferably, the oleaginous material is from about 4–8, and most preferably from about 5–7%, by weight of the composition.

The carboxylic copolymer contains a crosslinking monomer selected from the group consisting of triallylisocyanurate, triallyl trimellitate and glyoxal bis(diallyl acetal) in combination with an ethoxylated glyceride surfactant ester with an HLB value greater than 10.

A preferred carboxylic copolymer is a crosslinked carboxylic copolymer comprising (i) an unsaturated carboxylic acid;

(ii) an additional comonomer containing a polymerizable ethylenically unsaturated group;

(iii) a crosslinking monomer selected from the group consisting of triallylisocyanurate, triallyl trimellitate, and glyoxal bis(diallyl acetal); and (iv) an ethoxylated glyceride compound of the formula

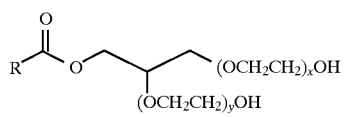

wherein R represents an alkyl group of from $C_8$ to $C_{18}$ and the sum of x+y is from 20 to 300.

The particularly preferred carboxylic copolymer comprises (a) from about 70% to 99% by weight, based on the weight of the carboxylic copolymer, of at least one unsaturated carboxylic acid;

(b) from about 0.2 to about 29%, based on the weight of the carboxylic copolymer, of a monomer containing a polymerizable ethylenically unsaturated group;

(c) from about 0.8% to about 1.2% by weight, based on the weight of the carboxylic copolymer, of at least one crosslinking monomer selected from the group consisting of triallylisocyanurate, triallyl trimellitate, and glyoxal bis(diallyl acetal); and (d) from about 0.1 to about 1.0% by weight, based on the weight of the carboxylic copolymer, of an ethoxylated glyceride of the formula

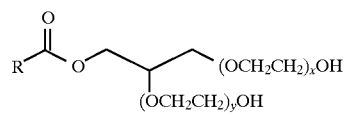

wherein R represents an alkyl group of from $C_8$ to $C_{18}$ and the sum of x+y is from 20 to 300.

In preferred embodiments, the polymerizable ethylenically unsaturated group is not selected from the group consisting of alkyl acrylates, alkyl methacrylates, acrylic acid esters derived from a polyalkylene glycol and methacrylic acid esters derived from a polyalkylene glycol.

The carboxylic copolymers used in the invention may be prepared according to the methods set forth in U.S. Pat. No. 5,416,158, which is incorporated herein in its entirety. Suitable carboxylic copolymers are commercially available from Rheox, Inc., Hightstown, N.J., USA, as Rheolate. The most preferred carboxylic copolymer is available from Rheox as Rheolate 5000.

During manufacture of the inventive compositions, the oleaginous material and the carboxylic copolymer are employed as a dispersion of the copolymer in the oleaginous material. Thus, some or all of the oleaginous material is combined with the carboxylic copolymer to produce a dispersion prior to combination with the remaining components of the composition. Preferred compositions comprise about 0.1 to about 3% of the carboxylic copolymer by weight based on the weight of the composition. Particularly preferred compositions of the invention comprise from about 0.5–1.5% of the copolymer by weight based on the weight of the composition. The preferred amount of copolymer is typically combined with the other components as a 20% by weight dispersion of the copolymer in the oleaginous material, preferably mineral oil. Combining the copolymer with the oleaginous material unexpectedly provides processing advantages. For example, the oleaginous material overcomes the need for high speed dispersion of the copolymer into the polyoxyethylene base.

In addition to the above components, the composition contains a neutralizer, typically a nitrogenous base, i.e., an amine. While the neutralizer is required for stability of the composition, it need not be combined initially with the other components but may be added later at the convenience of the formulator. However, in preferred embodiments of the invention, the neutralizer will be added at the time the other components are combined to yield the composition. Representative neutralizing agents include diisopropylamine, N,N-di-(2-ethylhexyl)amine, triamylamine, morpholine, and alkoxylated fatty amines. A particularly preferred neutralizing agent is an alkoxylated fatty amine having from about 10–18 carbon atoms and an average degree of ethoxylation of about 15.

The neutralizing agent is used in an amount sufficient to neutralize at least about 75% of the acid groups of the carboxylic copolymer, typically from about 0.1 to about 3% by weight of the composition. The resulting pH of the composition is generally from about 5.5 to 7.5.

The compositions of the invention may also contain pigments such as, for example, titanium dioxide, and dyes of various colors, e.g., red, yellow, or blue. The amount of dye or pigment will depend on the specific color desired;

amounts typically range from about 0.005 to about 5% by weight of the composition.

The compositions also function as carrier fill materials for an assortment of cosmetic materials, including fragrances, vitamins, etc. The fill material may be formulated as a cream or a lotion, e.g., an emulsion. The composition may also be manufactured to function as a "pepper spray", i.e., contain capsaicin.

The compositions are generally used as fill materials encapsulated in gelatin, preferably, soft gelatin capsules. The resulting capsules may be used as projectiles, i.e., as substitutes for standard lead or steel pellets used in recreational target shooting with small caliber air powered rifles and handguns. In this context, the capsules burst on impact and do not ricochet.

The soft elastic gelatin capsule shell used in the compositions of this invention may be formulated in accordance with conventional techniques for making filled, seamless, soft elastic gelatin capsules containing a fill material. See. e.g., Ebert, W. R., "Soft elastic gelatin capsules: a unique dosage form," Pharmaceutical Tech., October 1977; Stanley, J. P., "Soft Gelatin Capsules," The Theory and Practice of Industrial Pharmacy, 359–84 (Lea & Febiger ed. 1970). Optionally, the gelatin shell may contain preservatives such as mixed parabens, ordinarily methyl or propyl parabens, in about 4:1 ratio. The parabens may be incorporated in the shell formulation in minor proportions as compared to the total weight of the shell formulation. Conventional gelatin capsules utilize gelatin having a bloom value of about 140–200 although this amount may be varied. Using conventional techniques, the gelatin composition is mixed and melted under vacuum conditions. The capsules may be simultaneously formed and filled using a conventional method and apparatus such as those using rotary die process, as disclosed, for example, in U.S. Pat. Nos. 1,970,396; 2,288,327; and 2,318,718. Such equipment utilizes the rotary die process for encapsulating various fill materials in a gel mass.

The gelatin capsules may be formed into a substantially spherical shape and varying sizes depending upon the caliber of the air powered rifle or hand gun. For example, a substantially spherical gelatin capsule may be made with a slight modification to the diameter to accommodate a variety of small caliber air guns, i.e., .177, .22, .25, .32, .38, .45, etc. Preferably, the gelatin capsule will have a diameter ranging from about 0.16 inches to about 0.8 inches. Representative paintballs that may be prepared according to the invention include 68 caliber (0.675–0.700 inches in diameter) paintballs, 23 caliber (about 0.23 inches or 6 mm in diameter) paintballs, 40 caliber (about 0.40 inches in diameter) paintballs, and 50 and 60 caliber paintballs (about 0.5 and 0.6 inches in diameter respectively). Additionally, the gelatin capsules used in the instant invention will have a dry wall thickness in varying degrees, typically in the range of about 0.004 inches to about 0.013 inches and preferably about 0.007 inches to about 0.01 inches.

Thus, the fill material of the invention may be a water washable, nontoxic dye mixture. Any color or color combination may be employed but the particular choice of color selected is preferably bright and intense so as to be readily visible on a target at a reasonable distance for recreational target shooting. The fill material is desirably formulated in various colors to allow competition shooting by several participants against a single target. Approximate fill material quantities for substantially spherical capsules vary depending upon the diameter of the gelatin capsule. For example, the fill material quantities for capsules used in common small caliber guns such as .177, .22 and .25, which corresponds to the diameter in inches, may be approximately 0.03 ml, approximately 0.06 ml and approximately 0.12 ml, respectively. It will be apparent to thos skilled in the art that other quantities may be employed.

Typical compositions comprising blue, green, orange and red fill materials are illustrated below.

The general method for preparing the inventive fill material compositions is as follows.

Polyoxyalkylene glycol and glycerol are added to a suitable mixing vessel equipped with a disperser blade. Mixing is initiated and the mixing speed adjusted to the optimum that does not incorporate air in to the liquid mixture. A dispersion of the carboxylic copolymer in the oleaginous material is then added to the stirred PEG/glycerol mixture. Mixing continues until the mixture is clear, about 10 minutes.

After adding the carboxylic copolymer, water is added in an amount sufficient to hydrate the copolymer and the resulting mixture mixed for about 10 minutes.

Neutralizing agent is then added to the vessel and the resulting mixture stirred for about 15 minutes. At this point, any coloring material, i.e., dye or pigment, is added to the composition in the mixing vessel. The dye or pigment may be added with or without additional water, depending on the specific dye or pigment. For example, where the dye is water soluble, it is generally preferable to add the dye to the composition as an aqueous solution of the dye.

Pigment mixtures may be manufactured by dispersing a pigment such as titanium dioxide in polyoxyalkylene glycol, generally in a weight ratio of about 1:3 pigment:polyoxyalkylene glycol. Dye mixtures may be made by dissolving the dye in water to, for example, a concentration of about 25% by weight dye.

To ensure a product that is free of solids, the pigment and dye mixtures are passed through, for example, a 200 mesh screen, as they added to the mixing vessel. Mixing of the product is continued for an additional 5–10 minutes or until the color is well blended and uniform. The fill composition may then be encapsulated within gelatin capsules using the rotary die method.

The following examples demonstrate certain aspects of the present invention. However, it is to be understood that these examples are for illustrative purposes only and do not purport to be wholly definitive as to conditions and scope of this invention. It also should be appreciated that when typical reaction conditions (e.g., temperature, reaction times) have been given, the conditions which are both above and below these specified ranges can also be used, though generally less conveniently.

A further understanding of the invention may be obtained from the following nonlimiting examples. These examples were conducted at room temperature (about 23 degree(s) C. to about 28 degree(s) C.) and at atmospheric pressure. Each of the following compositions is prepared according to the method described above. All amounts are expressed in kilograms (kg), unless otherwise indicated. All temperatures are expressed in degrees Celsius (°C.).

EXAMPLE 1

Preparation and Encapsulation of Target Shooting Capsules Containing a Yellow Fill Material

| Component | Formulation 1 |
|---|---|
| Polyethylene glycol (added with glycerol) | 1160.00 |
| Polyethylene glycol (added with titanium dioxide) | 12.00 |
| glycerol | 41.5 |
| carboxylic copolymer, 20% dispersion in mineral oil | 104.00 |
| alkoxylated fatty amine having from about 10–18 carbon atoms and an average degree of ethoxylation of about 15 | 20.85 |
| FD & C Yellow No. 6 | 6.00 |
| purified water, USP | 41.72 |
| titanium dioxide | 3.93 |

Precise unit amounts of the fill compositions prepared above are filled and sealed into 68 caliber round soft gelatin capsules by the rotary die process and are dried for about 12–24 hours. The resulting capsules (paintballs) each contain about 2.5–3.0 ml of the composition.

Compositions 2 and 3 are prepared using the same procedure as Example 1 above.

EXAMPLE 2

Preparation and Encapsulation of Target Shooting Capsules Containing a Red Fill Material

| Component | Formulation 1 |
|---|---|
| Polyethylene glycol (total added with glycerol and titanium dioxide) | 1285.00 |
| glycerol | 39.50 |
| carboxylic copolymer, 20% dispersion in mineral oil | 10.42 |
| alkoxylated fatty amine having from about 10–18 carbon atoms and an average degree of ethoxylation of about 15 | 10.42 |
| FD & C Red No. 28 | 0.07 |
| FD & C Red No. 33 | 0.06 |
| purified water, USP | 41.50 |
| titanium dioxide | 3.04 |

Precise unit amounts of the fill compositions prepared above are filled and sealed into 68 caliber round soft gelatin capsules by the rotary die process and are dried for about 12–24 hours. The resulting capsules (paintballs) each contain about 2.5–3.0 ml of the composition.

EXAMPLE 3

Preparation and Encapsulation of Target Shooting Capsules Containing a White Fill Material

| Component | Formulation 1 |
|---|---|
| Polyethylene glycol (total added with glycerol and titanium dioxide) | 1282.00 |
| glycerol | 39.50 |
| carboxylic copolymer, 20% dispersion in mineral oil | 9.70 |
| alkoxylated fatty amine having from about 10–18 carbon atoms and an average degree of ethoxylation of about 15 | 9.70 |
| purified water, USP | 41.80 |
| titanium dioxide | 7.30 |

Precise unit amounts of the fill compositions prepared above are filled and sealed into 68 caliber round soft gelatin capsules by the rotary die process and are dried for about 12–24 hours. The resulting capsules (paintballs) each contain about 2.5–3.0 ml of the composition.

In the foregoing there has been provided a detailed description of preferred embodiments of the present invention for the purpose of illustration and not limitation. It is to be understood that all other modifications, ramifications and equivalents obvious to those having skill in the art based on this disclosure are intended to be within the scope of the invention as claimed.

What is claimed is:

1. A composition suitable for carrying pigment and encapsulation within gelatin capsules comprising, by weight of the composition:
   (a) from about 10–95% of a polyoxyalkylene glycol having a mean molecular weight of from about 200–500;
   (b) from about 1–5% of glycerol;
   (c) from about 1–85% of water;
   (d) 0.05 to about 10% of an oil;
   (e) from about 0.1–3% of a carboxylic copolymer containing a crosslinking monomer selected from the group consisting of triallylisocyanurate, triallyl trimellitate and glyoxal bis(diallyl acetal) in combination with an ethoxylated glyceride surfactant ester with an HLB value greater than 10; and
   (f) a neutralizing agent for the carboxylic polymer in an amount effective to neutralize at least about 75% of the carboxylic acid groups on the polymer.

2. A composition according to claim 1, further comprising a gelatin capsule encapsulating the composition.

3. A composition according to claim 2, further comprising a pigment.

4. A composition according to claim 1, wherein the copolymer is a crosslinked carboxylic copolymer comprising
   (i) an unsaturated carboxylic acid;
   (ii) an additional comonomer containing a polymerizable ethylenically unsaturated group;
   (iii) a crosslinking monomer selected from the group consisting of triallylisocyanurate, triallyl trimellitate, and glyoxal bis(diallyl acetal); and
   (iv) an ethoxylated glyceride compound of the formula

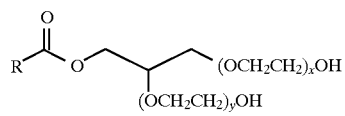

wherein R represents an alkyl group of from $C_8$ to $C_{18}$ and the sum of x+y is from 20 to 300.

5. A composition according to claim 1, where the composition comprises from about 80–95% by weight of the polyoxyalkylene glycol.

6. A composition according to claim 5, wherein the polyoxyalkylene glycol is polyethylene glycol having a mean molecular weight of about 300.

7. A composition according to claim 1, wherein the neutralizing agent is diisopropylamine, di-(2-ethylhexyl) amine, triamylamine, morpholine, or an alkoxylated fatty amine having from about 10–18 carbon atoms and an average degree of ethoxylation of about 15.

8. A composition according to claim 7, wherein the amount of the neutralizing agent is from about 0.1 to 2%.

9. A composition according to claim 8, wherein the neutralizing agent is an alkoxylated fatty amine having from about 10–18 carbon atoms and an average degree of ethoxylation of about 15.

10. A composition according to claim 9, wherein the oil is mineral oil.

11. A composition according to claim 10, wherein the carboxylic copolymer comprises
   (a) from about 70% to 99% by weight, based on the weight of the carboxylic copolymer, of at least one unsaturated carboxylic acid;
   (b) from about 0.2 to about 29%, based on the weight of the carboxylic copolymer, of a monomer containing a polymerizable ethylenically unsaturated group;
   (c) from about 0.8% to about 1.2% by weight, based on the weight of the carboxylic copolymer, of at least one crosslinking monomer selected from the group consisting of triallylisocyanurate, triallyl trimellitate, and glyoxal bis(diallyl acetal); and
   (d) from about 0.1 to about 1.0% by weight, based on the weight of the carboxylic copolymer, of an ethoxylated glyceride of the formula

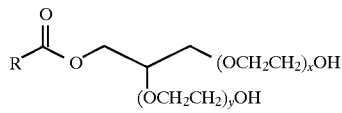

wherein R represents an alkyl group of from $C_8$ to $C_{18}$ and the sum of x+y is from 20 to 300.

12. A composition according to claim 1, wherein the oil is selected from $C_1$–$C_{22}$ straight or branched chain alkyl esters of straight or branched chain carboxylic acids having 12 to 22 carbon atoms, benzyl or $C_6$–$C_{22}$ straight or branched chain alkyl benzoates, glyceryl esters containing 8 to 22 carboxylic acid carbon atoms, sorbitan esters, straight or branched alkyl esters of alkoxylated fatty acid esters, fatty alcohols having from 10 to 22 carbon atoms, volatile hydrocarbons, semisolid hydrocarbons, and mineral oil.

13. A composition suitable for encapsulation within gelatin capsules comprising, by weight of the composition:
   (a) from about 82–87% of a polyethylene glycol having a mean molecular weight of from about 300;
   (b) from about 2–4% of glycerol;
   (c) from about 2–4% of water;
   (d) 5–7% of mineral oil or castor oil;
   (e) from about 1–2% of a carboxylic copolymer containing a crosslinking monomer selected from the group consisting of triallylisocyanurate, triallyl trimellitate and glyoxal bis(diallyl acetal) in combination with an ethoxylated glyceride surfactant ester with an HLB value greater than 10;
   (f) a neutralizing agent for the carboxylic polymer in an amount effective to neutralize at least about 75% of the carboxylic acid groups on the polymer; and
   (g) a dye or pigment.

14. A soft gelatin capsule containing the composition of claim 13.

15. A composition suitable for carrying pigment and encapsulation within gelatin capsules comprising, by weight of the composition:
   (a) from about 10–95% of a polyoxyalkylene glycol having a mean molecular weight of from about 200–500;
   (b) from about 1–5% of glycerol;
   (c) from about 1–85% of water;
   (d) 0.05 to about 10% of an oil;
   (e) from about 0.1–3% of a carboxylic copolymer comprising
       (i) an unsaturated carboxylic acid;
       (ii) an additional comonomer containing a polymerizable ethylenically unsaturated group, wherein the group is not selected from the group consisting of alkyl acrylates, alkyl methacrylates, acrylic acid esters derived from a polyalkylene glycol and methacrylic acid esters derived from a polyalkylene glycol;
       (iii) a crosslinking monomer selected from the group consisting of triallylisocyanurate, triallyl trimellitate, and glyoxal bis(diallyl acetal); and
       (iv) an ethoxylated glyceride compound of the formula

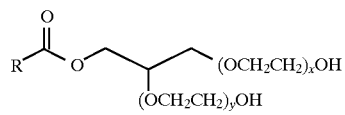

wherein R represents an alkyl group of from $C_8$ to $C_{18}$ and the sum of x+y is from 20 to 300; and
   (f) a neutralizing agent for the carboxylic polymer in an amount effective to neutralize at least about 75% of the carboxylic acid groups on the polymer.

16. A composition according to claim 15, further comprising a gelatin capsule encapsulating the composition.

17. A composition according to claim 16, further comprising a pigment.

18. A composition according to claim 17, where the composition comprises from about 80–95% by weight of the polyoxyalkylene glycol.

19. A composition according to claim 18, wherein the polyoxyalkylene glycol is polyethylene glycol having a mean molecular weight of about 300.

20. A composition according to claim 19, wherein the amount of the neutralizing agent is from about 0.1 to 2%; and the neutralizing agent is an alkoxylated fatty amine having from about 10–18 carbon atoms and an average degree of ethoxylation of about 15.

21. A composition according to claim 20, wherein the oil is mineral oil.

22. A composition according to claim 15, wherein the oil is selected from $C_1$–$C_{22}$ straight or branched chain alkyl esters of straight or branched chain carboxylic acids having 12 to 22 carbon atoms, benzyl or $C_6$–$C_{22}$ straight or branched chain alkyl benzoates, glyceryl esters containing 8 to 22 carboxylic acid carbon atoms, sorbitan esters, straight or branched alkyl esters of alkoxylated fatty acid esters, fatty alcohols having from 10 to 22 carbon atoms, volatile hydrocarbons, semisolid hydrocarbons, and mineral oil.

* * * * *